US006491644B1

(12) United States Patent
Vujanic et al.

(10) Patent No.: US 6,491,644 B1
(45) Date of Patent: Dec. 10, 2002

(54) IMPLANTABLE SOUND RECEPTOR FOR HEARING AIDS

(76) Inventors: Aleksandar Vujanic, Klosterneuburgerstrasse 102/6, A-1200 Vienna (AT); Robert Pavelka, Grünbeckgasse 15, A-2700 Wiener Neustadt (AT); Helmut Detter, Beethovengasse 12, A-2544 Leobersdorf (AT); Milos Tomic, Brace Srnic 13/15, 11000 Belgrade (YU)

( * ) Notice: Subject to any disclaimer, the term of this patent is extended or adjusted under 35 U.S.C. 154(b) by 0 days.

(21) Appl. No.: 09/830,195

(22) PCT Filed: Oct. 20, 1999

(86) PCT No.: PCT/AT99/00253

§ 371 (c)(1), (2), (4) Date: Apr. 23, 2001

(87) PCT Pub. No.: WO00/25550

PCT Pub. Date: May 4, 2000

(30) Foreign Application Priority Data

Oct. 23, 1998 (AT) .......................................... A1787/98

(51) Int. Cl.[7] .................................................. A61B 5/00

(52) U.S. Cl. ....................... 600/559; 600/310; 600/359; 73/655; 73/657; 356/348

(58) Field of Search ................................ 600/559, 310, 600/359; 73/655, 657, 643; 356/348, 349, 345

(56) References Cited

U.S. PATENT DOCUMENTS

| | | | | | |
|---|---|---|---|---|---|
| 4,339,954 | A | * | 7/1982 | Anson et al. | 73/657 |
| 4,689,820 | A | | 8/1987 | Kopke et al. | |
| 4,834,111 | A | * | 5/1989 | Khanna et al. | 128/774 |
| 5,295,191 | A | | 3/1994 | Van Vroenhoven | |
| 5,531,787 | A | | 7/1996 | Lesinski et al. | |
| 5,814,095 | A | * | 9/1998 | Muller et al. | 607/57 |
| 5,897,494 | A | * | 4/1999 | Flock et al. | 600/407 |
| 6,007,494 | A | * | 12/1999 | Zenner et al. | 600/559 |
| 6,048,320 | A | * | 4/2000 | Brainard, II | 600/559 |

FOREIGN PATENT DOCUMENTS

| | | | |
|---|---|---|---|
| EP | 0 831 674 A2 | 3/1998 | H04R/25/00 |
| JP | 02275909 | 11/1990 | G02B/6/255 |
| WO | WO 79/00841 | 10/1979 | G01H/9/00 |
| WO | WO 97/32385 | 9/1997 | H02J/7/35 |

* cited by examiner

*Primary Examiner*—Teresa Walberg
*Assistant Examiner*—Shawntina T. Fuqua
(74) *Attorney, Agent, or Firm*—Chapman and Cutler

(57) ABSTRACT

In an implantable sound receptor for hearing aids, the sound sensor is designed as an optical sensor (5) and arranged within the ear at a distance from the surface of a sound transmission part (3) capable of being excited to acoustic vibrations.

15 Claims, 3 Drawing Sheets

IMPLANTABLE SOUND RECEPTOR FOR HEARING AIDS

The invention relates to an implantable sound receptor for hearing aids, in particular for implantable hearing aids.

The majority of the known hearing aids is unsuitable for implantation. In principle, such hearing aids employ converters that are able to convert sound waves into electric signals. Such converters are known in the form of microphones and require appropriate membranes whose vibrations can be transformed into electric signals. The sensitivity of such microphones is largely influenced by the site of attachment and, above all, the size of the membrane. Acoustic vibrations can be picked up by pressure-sensitive membranes as is usually the case with microphone structures, or they can be detected by vibrometers receiving vibrations as acceleration signals or even as expansion measuring signals at deformations of vibrating structural components.

In U.S. Pat. No. 5,531,787, accelerometers in the form of piezo-resistive vibration sensors have been proposed. Alternatively, capacitive acceleration sensors are known to scan sound vibrations. Such miniaturized sensors have already been proposed for implantation in the region of the middle ear, whereby acoustic pressure waves generated in the region of the middle ear are scanned in the form of mechanical vibrations. In principle, such microphone structures are, however, relatively insensitive, because precise tuning to the acoustic impedance between the sensor and the tympanic cavity of the middle ear is not readily feasible.

Also other references such as, for instance, U.S. Pat. No. 3,557,775 have described microphones which may be implanted under the skin to receive audio signals, transmission being effected into the middle ear. Such arrangements, too, in terms of sensitivity are subjected to a number of not readily controllable foreign influences such as, for instance, the thickness of the skin and an unforeseeable formation of scar tissue and granulation tissue during the healing process, so that the sensitivity at the frequencies that are important to hearing will be attenuated in a variable and uncontrolled manner.

In principle, sounds that are heard are generated by sound waves, the pitch of a tone increasing with increasing frequency and the loudness increasing with increasing amplitude. In addition to tones and sounds, which constitute tonal mixtures, also a plurality of tones irregularly sounding simultaneously and having different frequencies and pitches are generated, which are heard as noises. By the natural hearing process, those sound waves are distinguished which are conducted from the auricle to the external auditory, thus causing the tympanic membrane to vibrate. The tympanic membrane is grown together with the hammer shank, whereby further transmission is effected via the auditory ossicles through the base of the stapes to the perilymphatic liquid, which causes the organ of Corti to vibrate. The excitation of the hair cells in the organ of Corti cause the generation of nerve impulses which are conducted by the auditory nerve into the brain, where they will be distinguished consciously.

The tympanic membrane functions as a pressure receiver and has a diameter of about 1 cm. If microphones having such large membranes are to be used to receive sound waves, such microphones will hardly be suitable for implantation, since the space required therefor is not available in the region of the ear.

Impaired hearing may have various causes. In a considerable number of hearing defects, the mechanical part of the vibration transmission from the tympanic membrane via the auditory ossicles to the liquid in the *scala vestibuli* is intact. It has, therefore, been already proposed to connect a vibration sensor directly with the membrane or the auditory ossicles in order to accordingly convert into electric signals, and amplify, the vibrations brought about by sound. Such an intervention has the drawback that, on the one hand, relatively high operating expenditures are involved in the arrangement of such sensors and, on the other hand, every mechanical influence of vibrating parts and, in particular, the damping of such vibrating parts, considerably influences the vibration behavior of those parts such that correct signals as are generated during the natural hearing process will not be obtained in that case, either. In principle, the miniaturization of microphones results in a decrease of sensitivity, this being not least due to the missing tuning of the acoustic impedance between microphone and ambient air. Even if this effect can be improved by implanting the microphone under the skin, this will lead to an alteration of the scannable frequency range with, in particular, higher frequencies being more strongly attenuated. Also other mechanical sound wave receptors such as, for instance, tubes filled with fluids, lead to an attenuation due to the viscosity of the used fluid, whereby rigid acoustic couplers, in general, are unsuitable for implantation.

The invention aims to provide a small-structured implantable sound receptor which avoids the drawbacks of the known sound receptors while maintaining the acoustic sensitivity on a constantly high level over the entire frequency range that is essential to hearing, i.e., from about 100 Hz to more than 10 kHz. The invention, furthermore, aims to keep the structural dimensions so small as to enable its implantation in the middle ear and/or the adjacent mastoid antrum. The surgical intervention preferably is to be reversible, whereby no substantial deterioration of the previously existing audition is to occur at a functional failure of the sound receptor. In a restrictive manner, an operative interruption of the sound transmission chain may, however, be required as a function of the employed actuator and its point of application, in order to avoid feedbacks. In addition to these demands set on an implantable sound receptor, also the energy consumption of the sound receptor and of a consecutive evaluation circuit is, of course, to be kept so low as to enable a total implantation due to miniaturization.

To solve this object, the implantable sound receptor for implantable hearing aids according to the invention essentially consists in that the sound sensor is designed as an optical sensor for vibration and distance measurements and is arranged within the ear at a distance from the surface of a sound transmission part capable of being excited to acoustic vibrations. Due to the fact that, as opposed to the hitherto applied physical principles of sound receptors for hearing aids, contactless scanning by means of an optical scanner has been proposed, it is actually feasible to measure the vibrations that are physiologically transmitted by the tympanic membrane and the auditory ossicles. The contactless configuration prevents undesired side effects of an attenuation of such vibrating auditory ossicles and the tympanic membrane and enables the unhampered use of the relatively large vibration pickup surface of the tympanic membrane for measuring, so that a considerably higher sensitivity can actually be attained than would be feasible with accordingly smaller membranes. Due to the fact that the optical sensor is arranged or arrangeable within the ear at a distance from the surface of a vibration transmission part capable of being excited to vibrations, it is ensured that any attenuation of the vibrations of such vibration transmission parts capable of being excited to vibrations will be reliably excluded and the use of optical sensors will allow the use of extremely small-structured sensors.

By optical sensors, sensors that do not necessarily use visible light are to be understood in this context. For optical sensors, electromagnetic waves in a relatively wide frequency range that goes beyond the spectrum of visible light may be used. As transmitters, laser diodes may, in particular, be used both in the infrared and ultraviolet ranges of radiation and in the visible range, as long as the vibrating surface to be measured is sufficiently reflective in the range of the irradiated wavelength. Optical sensors, thus, in the first place serve to measure the optical parameters of the reflected portions of the emitted signal, the evaluation of the signals of the sound receptor advantageously being effected in a manner that the optical sensor is connected with an interferometer to evaluate the amplitude, the frequency and/or the relative phase relationship of the vibration of the scanned part. The use of the interferometer principle, for which various configurations are known, allows the reliable detection of even slight amplitudes of natural vibrations in the region of the auditary ossicles in a contactless manner. The range to be detected extends from amplitudes of $10^{-11}$ m to approximately $10^{-5}$ m, whereby higher amplitudes than approximately $5\times10^{-5}$ m as may be observed at a sound irradiation of about 120 dB, as a rule, will not be taken into consideration for further measurements since these may already cause damage to the internal ear.

The vibrations of the auditory ossicles and the tympanic membrane as observed upon excitation by acoustic waves, however, are overlaid in the ear also by a low-frequency quasi-static or slow dislocation of the tympanic membrane and the ossicles, which is due to differences in the air pressure or the pressure prevailing within the internal ear. Such low-frequency dislocations are caused, for instance, by changes in the air pressure when going by a lift, cable car or airplane, whereby important low-frequency deviations are also observed when blowing one's nose due to the sudden opening of the auditory tube. Such low-frequency dislocations in terms of amplitude may be higher by a factor of at least $10^2$ than the maximum amplitudes occurring at the physiological exposure to sonic waves. Thus, optical sensors must be arranged in a manner that no contact with the part to be scanned will occur even during such dislocations, and the configuration according to the invention is, therefore, devised such that the optical sensor is arranged at a distance from the scanned part that is larger than the maximum dislocation of the scanned part occurring in the direction of the sensor, and/or is adjustably retained at a collision-preventing distance. The use of an adjustable retention means to maintain a defined distance may comprise a servomotor, the adjustment signals of the servo-motor being applied to determining the acoustic vibrations and the adjustment movements themselves being triggered by the optical sensor.

Optical scanning in a particularly simple manner is feasible in that the optical sensor cooperates with at least one light or laser diode and the reflected signals are fed to at least one optoelectronic switching component, for instance a photodiode, of an electronic evaluation circuit via fibers of waveguides, in particular optical waveguides. The sensor part to be implanted in the middle ear or in the epitympanum or epitympanic recess in such a configuration is restricted to the relatively small free end of the optical waveguide via which the optical signals are fed and the reflected signals are picked up. In the beam path also one or several optical systems such as, for instance, lenses, beam splitters, prisms, mirrors or the like may, of course, be arranged depending on the orientation and structure of the device, in order to render measurements accordingly precise or locate the same.

The evaluation circuit subsequently must provide an accordingly amplified signal to the stimulus of the auditory nerve, the configuration in this respect advantageously being devised such that the evaluation circuit generates signals for the electromechanical vibration generator, and/or the electric stimulation of the organ of Corti and/or the auditory nerve and/or the brain stem, and comprises connections for the respective signal lines.

In order to prevent the free end of the optical sensor to be implanted preferably in the middle ear from being subjected to measuring errors or sensitivity fluctuations caused by turbidities, the configuration advantageously is devised such that the free ends of the optical sensor are provided with a cell-growth-inhibiting coating.

In order to suppress fading effects which are to be observed in the interferometric evaluation and overlay of low-frequency dislocations, it is particularly advantageous to detect also the relative phase position of the vibration of the scanned part in addition to evaluating its amplitude and frequency. To this end, it may advantageously be proceeded in a manner that at least two signals are fed to the evaluation circuit to determine the phase relationship, the determination of the phase relationship in a known manner enabling the respective active or passive stabilization as a function of the type of interferometer used and the circuit arrangement of the evaluation circuit chosen. Depending on the arrangement, the optimum sensitivity of the optical sensor is based on a predetermined operating point pregiven by a defined distance relative to the surface to be measured. Low-frequency dislocations of the parts to be scanned naturally may lead to the leaving of that optimum operating point or even to the occurrence of a phase shift or phase reversal. Such undesired side effects, which may cause "fading" of the measured signal advantageously may be eliminated in that the evaluation circuit comprises a stabilizing circuit to compensate for the shift of the operating point of the interferometer by low-frequency dislocations of the scanned part. Alternatively or additionally, appropriate compensation may be safeguarded in that a sensor for the detection of the distance of the part to be scanned from the optical sensor is additionally provided. The stabilization of interferometric signals may be effected in a particularly simple manner by comparison with a reference signal or by measuring a plurality of signals, whereby polarizing beam splitters may be arranged in the beam path and the signals may be detected independently and by different photodiodes. Conclusions as to the correct phase position may be drawn also from a mathematical analysis of the shape of the measuring signal, frequency comparisons and, in particular, the evaluation of higher-order vibrations in the stabilizing circuit being applicable to this end.

In order to enable the precise positioning of the sound receptor, the configuration in a particularly simple manner is devised such that the free end of the optical sensor is adjustably fixed in a bearing block and/or connected with an adjustment drive, thus safeguarding the precise orientation and precise positioning relative to the surface of the part whose vibration is to be measured.

The actual configuration of the interferometer subsequently calls for the respectively preferred algorithms for evaluation. Interferometers in this regard may be configured according to any desired mode of construction such as, for instance, as a Michelson, Fabry-Perot or Fizeau interferometer, suitable stabilizing algorithms being described, for instance, in the article by K. P. Koo, A. B.

Tveten, A. Dandridge, "Passive stabilization scheme for fiber interferometers using (3×3) fiber directional couplers", in Appl.Phys.Lett., Vol. 41, No. 7, pp. 616–18, 1982; G. Schmitt, W. Wenzel, K. Dolde, "Integrated optical 3×3 coupler on LiNbO3: Comparison between theory and experiment", Proc.SPIE, Vol. 1141, 5$^{th}$ European Conference on Integrated Optics: ECIO 89, pp. 67–71, 1989, R. Fuest, N. Fabricius, U. Hollenbach, B. Wolf, "Interferometric displacement sensor realized with a planar 3×3 directional coupler in glass", Proc.SPIE, Vol. 1794, Integrated Optical Circuits II, pp. 352–365, 1992; L. Changchun, L. Fei, "Passive Interferometric Optical Fiber Sensor Using 3×3 Directional Coupler", Proc.SPIE, Vol. 2895, pp. 565–571, 1995. Other proposals are to be found, i.a., in A. Dandridge, A. B. Tveten, T. G. Giallorenzi, "Homodyne Demodulation Scheme for Fiber Optic Sensors Using Phase Generated Carrier", IEEE J.Quantum Elec., Vol. QE-18, No. 10, pp. 1647–1653, 1982, J. H. Cole, B. A. Danver and J. A. Bucaro, "Synthetic Heterodyne Interferometric Demodulation", IEEE J.Quantum Elec., Vol. QE-18, No. 4, pp. 694–697, 1982.

In the following, the invention will be explained in more detail by way of an exemplary embodiment schematically illustrated in the drawing. Therein, FIG. 1 is a cross section through the human ear, in which the arrangement of a sensor in the middle ear region or attic is illustrated;

Figure 1:
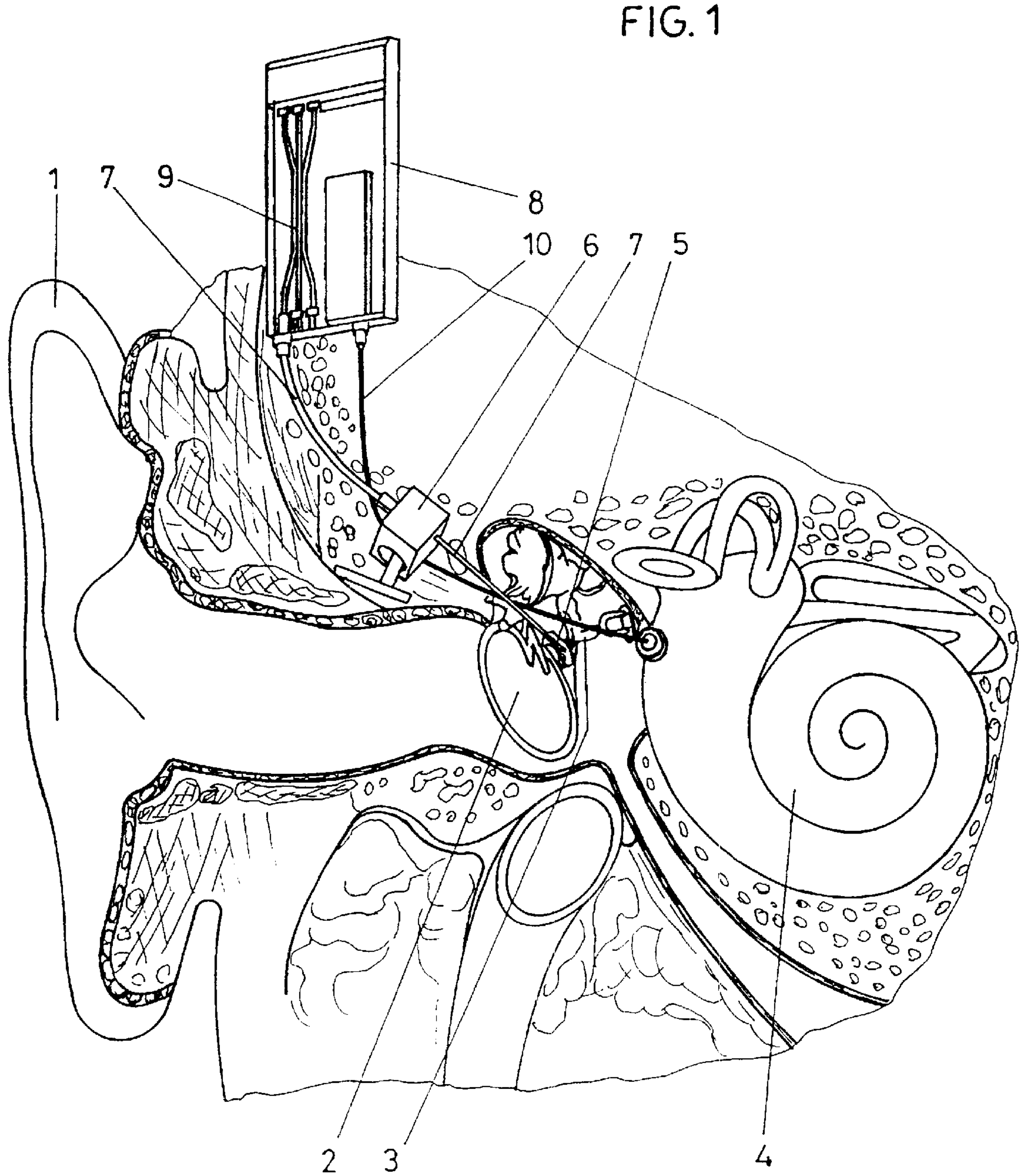

In FIG. 1, the auricle of an ear is denoted by 1. Acoustic vibrations subsequently get to the membrane denoted by 2, i.e., the tympanic membrane, which cooperates with the auditory ossicles. The auditory ossicles together are denoted by reference numeral 3.

The auditory ossicles are located in the region of the middle ear. The cochlea is denoted by 4.

The contactless sensor adapted to scan the vibrations of the auditory ossicles 3 is implanted in the mastoid antrum, projecting with its tip into the attic and, via the opened chorda facialis angle, into the middle ear. It has a free end 5 which is inserted in a stable sleeve (sheath) orientably held in a bearing block 6. The bearing block 6 may be fixed in the mastoid antrum or the surrounding cranial bone, the free end of the optical sensor being substantially comprised of the free end of a fiber-optical light guide or waveguide 7. The tip advantageously contains an optical system comprised, for instance, of lenses, beam guides, prisms, mirrors or the like, or a bend of the fiber tip to deflect the optical beam path in order to enable registration from the optimum direction. The fiber-optical waveguide 7 is connected to an optoelectronic evaluation circuit 8 in which an interferometer 9 is arranged.

The optoelectronic evaluation circuit 8 may additionally contain in its casing an energy supply means in the form of a battery, whereby the circuit arrangement includes respective input-output circuits, a hearing aid electronics comprising means for signal processing, noise suppression, acoustic limitation, etc., or these circuits required for the actuator are housed in a separate implantable component which is coupled by an electric cable. The electric signals may, thus, be transmitted to the cochlea 4 via lines 10. With an accordingly smaller dimensioned optoelectronic evaluation circuit 8, also this optoelectronic evaluation circuit may be implanted as a whole. The type of transmission of the evaluated signals to the internal ear or the auditory nerve is of minor importance to the type of scanning of the vibrations. The actuator may be one that sets the auditory ossicles or the perilymph directly in acoustic vibrations, or a cochlea implant which stimulates the auditory nerve electrically, or a brain stem implant directly stimulating the brain stem electrically.

Figure 2:
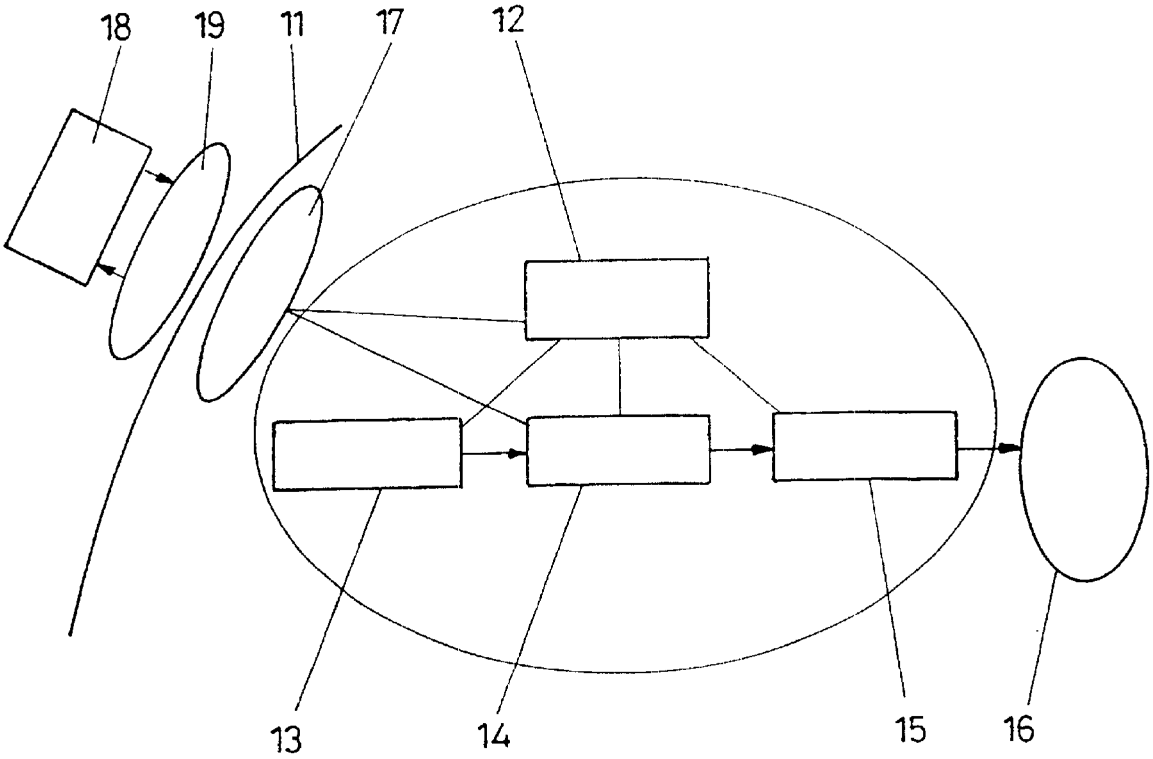
FIG. 2 is a block diagram of a totally implanted hearing aid.

A block diagram of the circuit arrangement chosen in this context is depicted in FIG. 2. The skin covering the implant is schematically indicated by 11, the evaluation circuit and optionally the energy supply being arranged subcutaneously in the region of the middle ear, the mastoid antrum or on the cranial bone. The battery is schematically indicated by 12, the optical sensor and the interferometer by 13, the evaluation electronics by 14 and the actuating member via which the signals, upon processing in the hearing aid electronics, are transmitted to an electromechanical amplifier of the perilymph vibrations or to a cochlea implant or a brain stem implant (denoted by 16), respectively, by 15. The energy supply by the battery 12 may preferably be realized by means of a rechargeable battery, to which end additional inputs for an induction coil 17 are provided in order to enable recharging of the battery and optionally programming of the electronics by the aid of an external charging and control unit 18. Transmission in this case may be effected in a contactless manner, via an induction coil 19 of the control and charging unit 18, which may be coupled with the subcutaneous induction coil 17.

Figure 3:
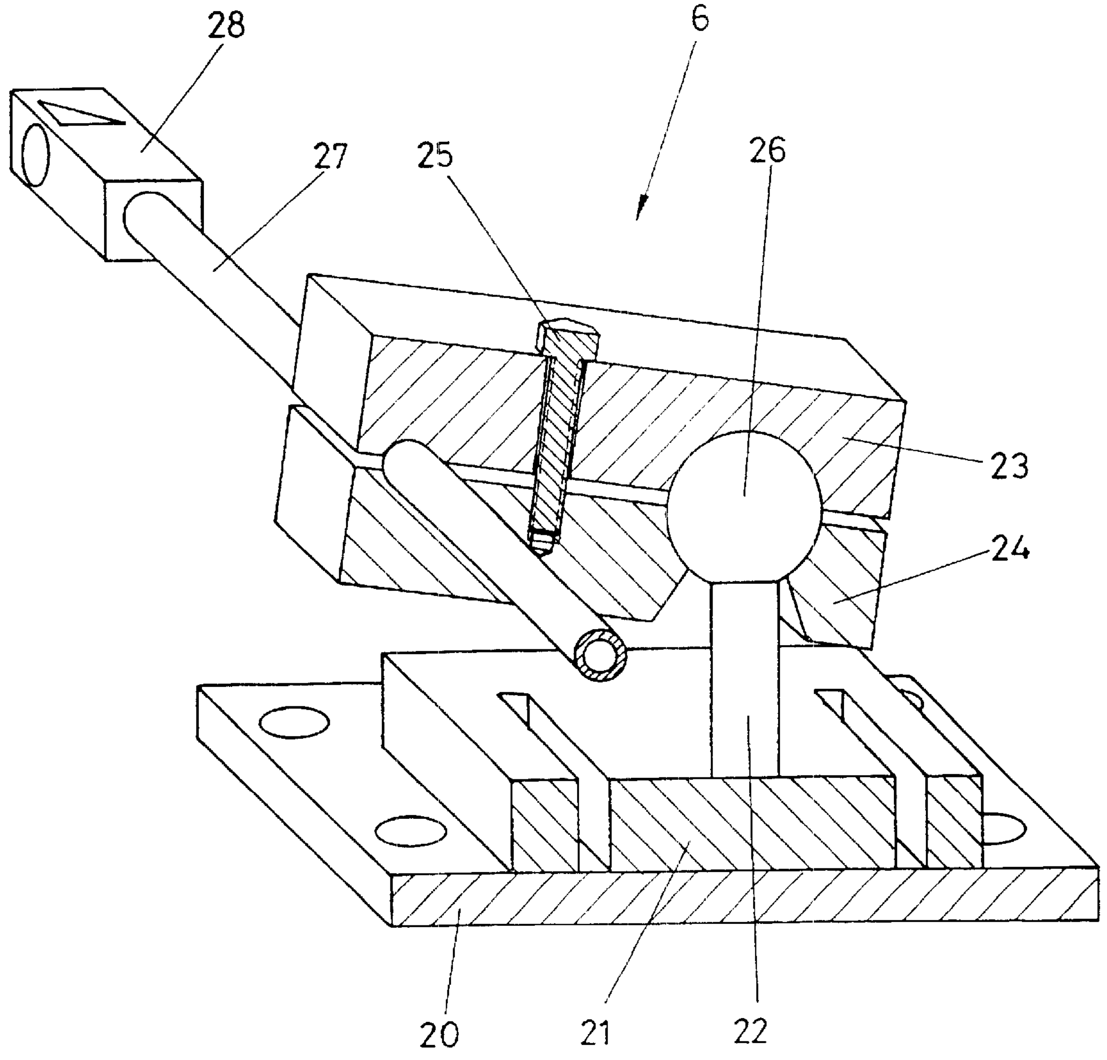
FIG. 3 is a schematically represented retention means for the waveguide, or waveguide covered by a rigid sheath, in the mastoid antrum.

The illustration according to FIG. 3 schematically elucidates a possible configuration of a bearing block 6. A base plate 20 carrying a displaceable carriage 21 is fixed in the mastoid antrum. The displaceable carriage 21 carries a ball-ended gudgeon 22 to which a clamp with cheeks 23 and 24 is orientably fixed by means of a clamping screw 25. The cheeks 23 and 24 have ball-shaped bearing surfaces which are pivotably orientable on the circumference of the ball 26 of the ball-ended gudgeon 22 so as to enable precise adjustment in various space coordinates.

An optical waveguide 27 is placed into a defined position by the cheeks 23 and 24, its free end 28 being so oriented as to be able to receive the reflected radiation from a vibrating part of the internal ear. In the free end 28 of the optical waveguide 27 may be installed optical systems, prisms, mirrors or the like, for the deflection of the beam path, if desired. Via the optical waveguide 27, the signals get to the optoelectronic evaluation circuit containing the interferometer.

The arrangement of such a structural component suitable to adjust the free end 28 of an optical waveguide 27 may be realized in a simple manner in the relatively large mastoid antrum. Fine adjustment serves to provide the desired distance and desired orientation relative to the surface, of the vibrating part of the middle ear to be measured. In principle, it is, however, also feasible with an appropriate orientation and accordingly higher radiation performance, to use a larger distance for scanning, whereby also optical expenses may be raised. Measurements also may be carried out, for instance, from the mastoid antrum directly into the attic with scanning being effected, for instance, on the incus head. On account of the type of vibration transmission involved herein, it must, however, be taken into consideration that the individual auditory ossicles partially oscillate at mutually opposite phases in respect to the vibration of the tympanic membrane. Scanning on sites with slighter quasi-static dislocations offers the advantage that the extent of a linear dislocation due to pressure differences is substantially reduced as compared to the measuring distance such that the expenses involved in the stabilization of the phase position and the elimination of the fading effect will be reduced accordingly.

What is claimed is:

1. An implantable sound receptor for hearing aids, comprising:

a sound sensor designed as an optical sensor for vibration and distance measurements, said sensor mountable within an ear at a distance from a surface of a sound transmission part sensible to acoustic vibrations, the optical sensor being arranged at a distance from a scanned part that is larger than a maximum dislocation of the scanned part occurring in a direction of a front face of the sensor, and is adjustably retained at a collision-preventing distance;

an electronic evaluation circuit connected with said optical sensor in order to generate signals for electromechanical vibration generators, and/or for stimulation of the organ of Corti and/or the auditory nerves, and/or the brain stem, said evaluation circuit including connections for respective signal lines; and a stabilizing circuit cooperating with said evaluation circuit to compensate for a shift of an operating point of an interferometer by low-frequency vibrations of the scanned part.

2. The implantable sound receptor according to claim 1, wherein the optical sensor cooperates with at least one light diode and reflected signals are fed to at least one optoelectronic switching component of an electronic evaluation circuit via fibers of waveguides, in particular optical waveguides.

3. The implantable sound receptor according to claim 1, wherein the optical sensor cooperates with at least one laser diode and reflected signals are fed to at least one optoelectronic switching component of an electronic evaluation circuit by means of optical waveguides.

4. The implantable sound receptor according to claim 2, wherein the optoelectronic switching component is a photodiode.

5. The implantable sound receptor according to claim 1, wherein the optical sensor is connected with said interferometer to evaluate at least one of parameters of the vibration of the scanned part, said parameters being amplitude, frequency and relative phase position.

6. The implantable sound receptor according to claim 2, wherein the optical sensor is connected with said interferometer to evaluate at least one of parameters of the vibration of the scanned part, said parameters being amplitude, frequency and relative phase position.

7. The implantable sound receptor according to claim 1, wherein the evaluation circuit receives at least two signals for determination of vibration parameters of the scanned part.

8. The implantable sound receptor according to claim 5, wherein the evaluation circuit receives at least two signals for determination of vibration parameters of the scanned part.

9. The implantable sound receptor according to claim 6, wherein the evaluation circuit receives at least two signals for determination of vibration parameters of the scanned part.

10. The implantable sound receptor according to claim 1, wherein the optical sensor having a free end, and the free end is provided with a cell-growtb-inhibiting coating.

11. The implantable sound receptor according to claim 10, wherein the free end of the optical sensor is adjustably fixed in a bearing block.

12. The implantable sound receptor according to claim 11, wherein the free end of the optical sensor is further connected to an adjustment drive.

13. The implantable sound receptor according to claim 2, wherein the optical sensor having a free end, and the free end is provided with a cell-growth-inhibiting coating.

14. The implantable sound receptor according to claim 13, wherein the free end of the optical sensor is adjustably fixed in a bearing block and/or connected with an adjustment drive.

15. The implantable sound receptor according to claim 14, wherein the free end of the optical sensor is further connected to an adjustment drive.

* * * * *